United States Patent
Jayaraman

[19]

[11] Patent Number: 5,855,597
[45] Date of Patent: Jan. 5, 1999

[54] STENT VALVE AND STENT GRAFT FOR PERCUTANEOUS SURGERY

[75] Inventor: Swaminathan Jayaraman, Malleswaram, India

[73] Assignee: Iowa-India Investments Co. Limited, United Kingdom

[21] Appl. No.: 852,240

[22] Filed: May 7, 1997

[51] Int. Cl.⁶ .................................................. A61F 2/06
[52] U.S. Cl. ............................................................ 623/1
[58] Field of Search ........................................... 623/1, 12

[56] References Cited

U.S. PATENT DOCUMENTS

| | | |
|---|---|---|
| 3,671,979 | 6/1972 | Moulopoulos . |
| 4,056,854 | 11/1977 | Boretos et al. . |
| 4,297,749 | 11/1981 | Davis et al. . |
| 5,332,402 | 7/1994 | Teitelbaum . |
| 5,397,355 | 3/1995 | Marin ........................................... 623/1 |
| 5,507,771 | 4/1996 | Gianturco ..................................... 623/1 |
| 5,522,881 | 6/1996 | Lentz ........................................... 623/1 |
| 5,618,301 | 4/1997 | Hauenstein ................................... 623/1 |
| 5,769,887 | 6/1998 | Brown .......................................... 623/1 |
| 5,776,161 | 7/1998 | Globerman ................................... 623/1 |

*Primary Examiner*—Michael J. Milano
*Attorney, Agent, or Firm*—James E. Larson; Larson & Larson, P.A

[57] ABSTRACT

A star-shaped stent and replacement valve or replacement graft for use in repairing a damaged cardiac valve includes two to eight star-shaped members interconnected into a "chain". Once this "chain" has been created through interconnection of the star-shaped members, a central opening through all of the interconnected star-shaped members receives a replacement aortic valve tri-cuspid made of any suitable flexible and bio-compatible material. A catheter delivery system is used to deliver the stent with the aortic valve tri-cuspid to the desired site. The star-shaped stents are made by using a laser to cut out a plurality of flat star-shaped members with a plurality of outwardly and inwardly directed points. The outwardly directed points are bent so that they face away from a plane defined by the inwardly directed points and then a series of such stents are fastened together in a chain.

27 Claims, 10 Drawing Sheets

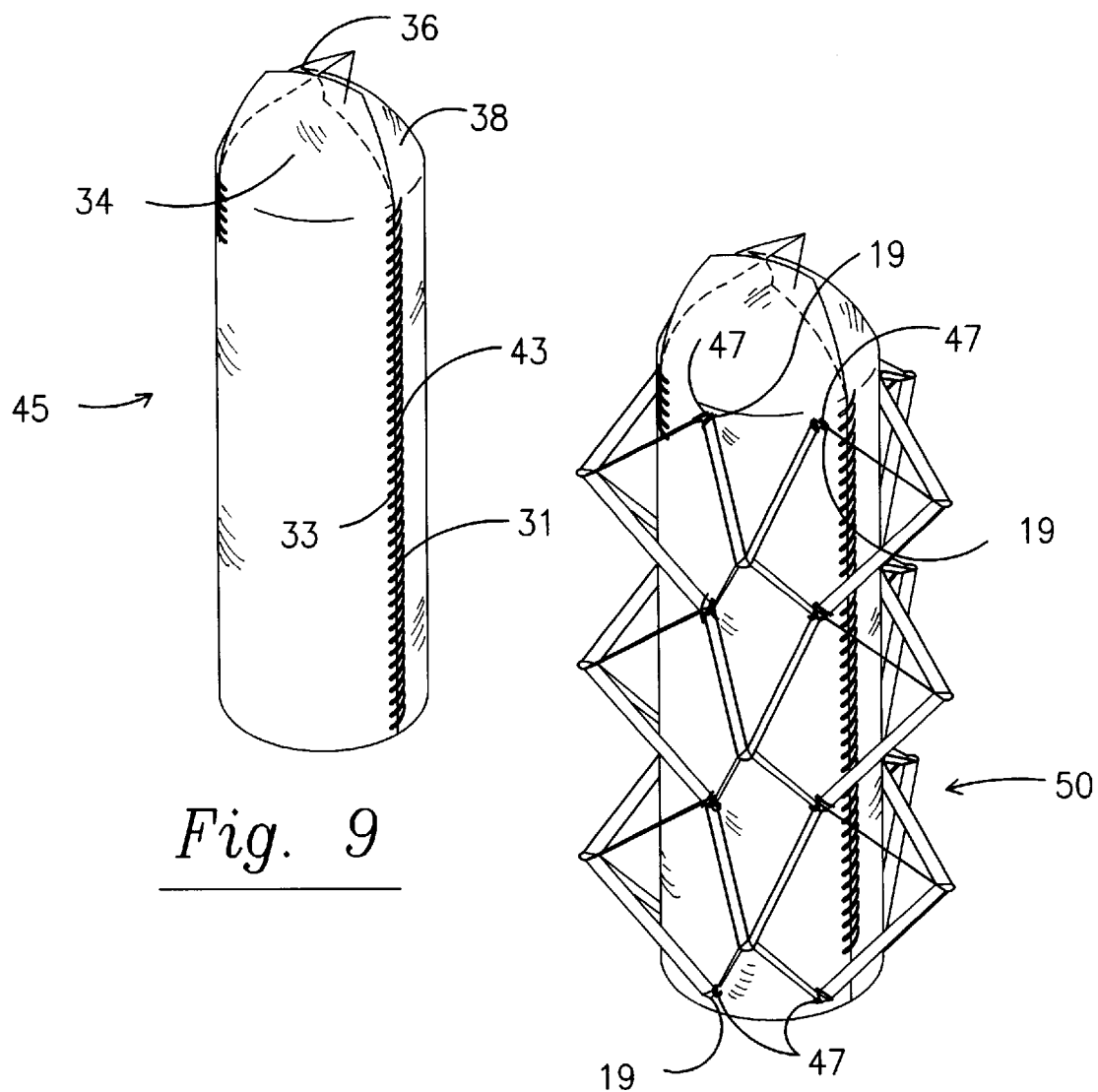

5,855,597

STENT VALVE AND STENT GRAFT FOR PERCUTANEOUS SURGERY

BACKGROUND OF THE INVENTION

The present invention relates to a star-shaped stent and replacement valve and replacement graft for use in repairing a damaged cardiac valve. In the prior art, stents are known and are employed, usually, to maintain a blood vessel or other body passageway open and free from obstruction.

Applicant is aware of the following U.S. Pat. Nos.:

U.S. Pat. No. 3,671,979 to Moulopoulos

U.S. Pat. No. 4,056,854 to Boretos et al.

U.S. Pat. No. 4,297,749 to Davis et al.

U.S. Pat. No. 5,332,402 to Teitelbaum.

These patents relate to repairs to and replacements for cardiac valves. However, none of these references teaches the features and aspects of the present invention.

SUMMARY OF THE INVENTION

The present invention relates to a star-shaped stent and replacement valve for use in repairing a damaged cardiac valve. The present invention includes the following interrelated objects, aspects and features:

(1) In a first aspect, the inventive stent is made in a star-shape by cutting it from a flat metal sheet, preferably in the range of 25 to 50 mils in thickness. The metal sheet may be stainless steel, titanium, elgiloy or heat activatable metal such as NITINOL. The star shape of the stent includes a thin outline of a star with the center open. Thus, for example, where the star has five outwardly directed points, the same star has five inwardly directed points.

(2) The inventive stent is created by interconnecting from two to eight of these star-shaped members into a "chain".

(3) Once this "chain" has been created through interconnection of the star-shaped members in a manner to be described in greater detail hereinafter, a central opening through all of the interconnected star-shaped members receives a replacement aortic valve tri-cuspid made of any suitable flexible and bio-compatible material. A catheter delivery system is used to deliver the stent with the aortic valve tri-cuspid to the desired site where it is expanded into position. The chain of stents can be sutured outside a knitted, woven or polymeric extruded tube to replace a diseased portion of an artery in various locations, including the heart.

(4) In the preferred embodiment, each star-shaped member has five points. However, if desired, any number of points from two to five may be suitably employed.

Accordingly, it is a first object of the present invention to provide a star-shaped stent and replacement valve for use in repairing a damaged cardiac valve.

It is a further object of the present invention to provide such a device including a stent made of a plurality of interconnected star-shaped members.

It is a still further object of the present invention to provide such a device including a replacement aortic valve tri-cuspid inserted within the star-shaped members and attached thereto.

It is a still further object of the present invention to provide a stent-graft for percutaneous replacement in the body.

These and other objects, aspects and features of the present invention will be better understood from the following detailed description of the preferred embodiment when read in conjunction with the appended drawing figures.

BRIEF DESCRIPTION OF THE DRAWINGS

FIG. 9 shows the tube of FIG. 8 but with the slitted end thereof folded in three overlapping pieces to form the tri-cuspid.

FIG. 10 shows the device of FIG. 9 inserted within the three pairs of star-shaped members of FIG. 6 and affixed thereto to form an integral assembly.

FIG. 21 shows the patch on the inside of the conduit after it is turned outside-in.

SPECIFIC DESCRIPTION OF THE PREFERRED EMBODIMENT

Figure 1:
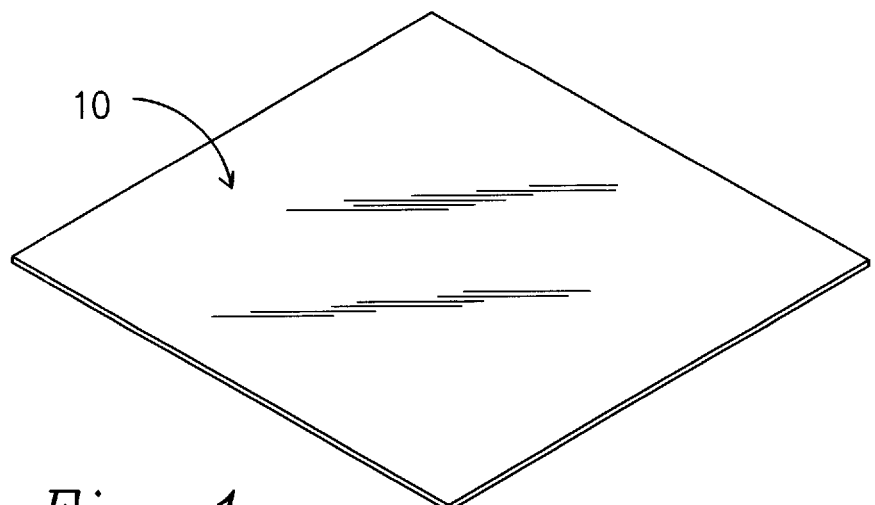
FIG. 1 shows a perspective view of a thin metal sheet from which a star-shaped member may be cut.
Figure 2:
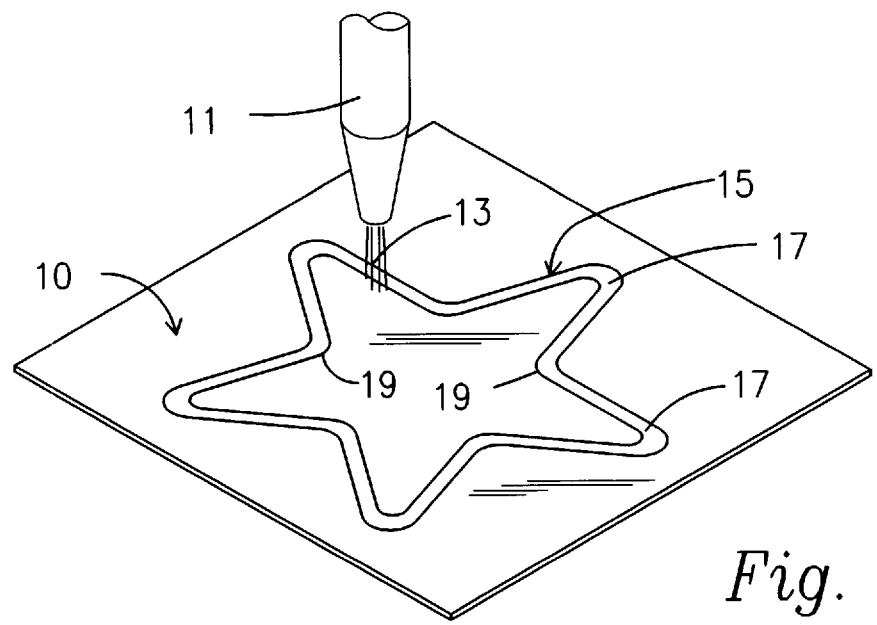
FIG. 2 shows a perspective view of the use of a laser saw to cut a star-shaped member from the metal sheet of FIG. 1.

With reference, first, to FIG. 1, a metal sheet is generally designated by the reference numeral 10 and is of a uniform thickness, preferably in the range of 25 to 50 mils. With reference to FIG. 2, a laser saw 11 emits a beam 13 that may be used to cut a star-shaped member 15 from the sheet 10. Other processes for cutting out a star-shaped member 15 includes chemical etching, electrolysis and other selective removal techniques. As seen in FIG. 2, the star-shaped member 15 includes five outwardly directed points 17 and five inwardly directed points 19. The center of the star-shaped member 15 is open as best seen with reference to FIG. 3.

Figures 3, 4:
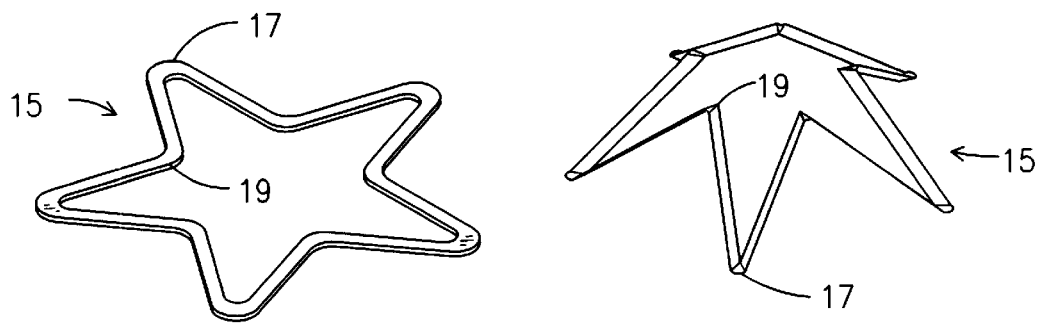
FIG. 3 shows a star-shaped member that has been cut from the metal sheet as illustrated in FIGS. 1 and 2.
FIG. 4 shows the star-shaped member of FIG. 3 flexed to a position facilitating attachment to another star-shaped member.

With reference to FIG. 4, given the thinness of the metallic material used to create the star-shaped member 15, it may easily be flexed to assume the configuration shown in FIG. 4 with the outwardly directed points 17 sloping downwardly with respect to a plane defined by the inwardly directed points 19.

Figures 5, 6:
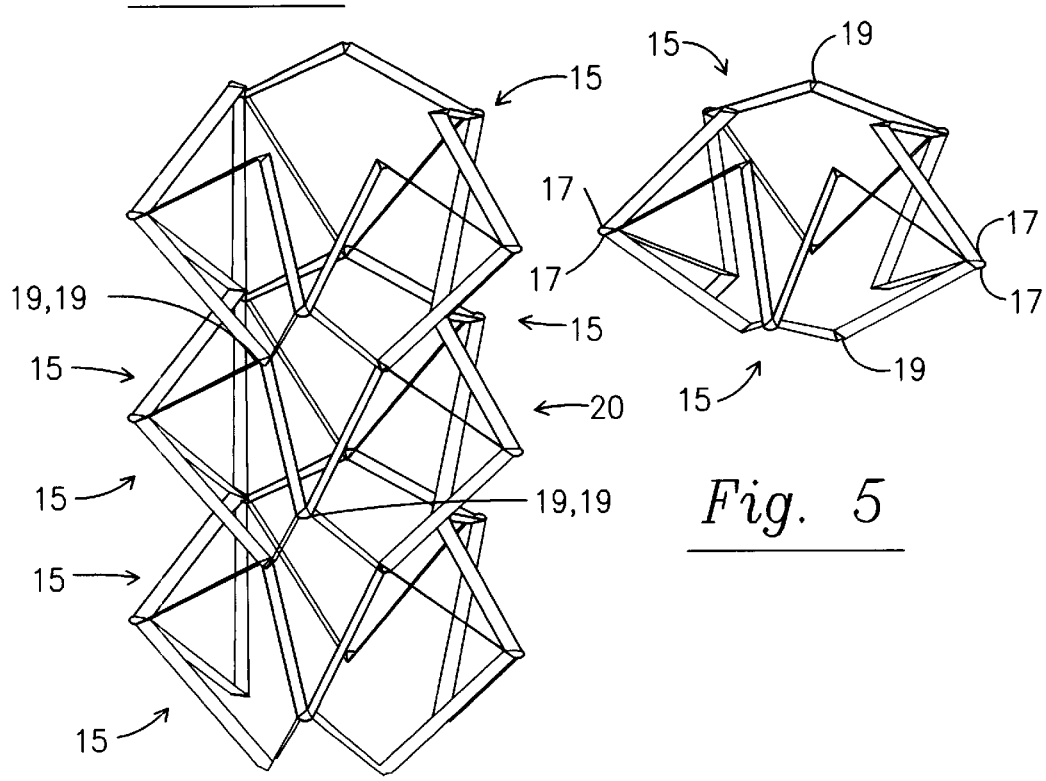
FIG. 5 shows two such star-shaped members attached together by their outwardly directed points.
FIG. 6 shows three pairs of star-shaped members such as the pair shown in FIG. 5, interconnected together with adjacent such pairs being connected by their respective star-shaped member inwardly directed points.
Figure 7:
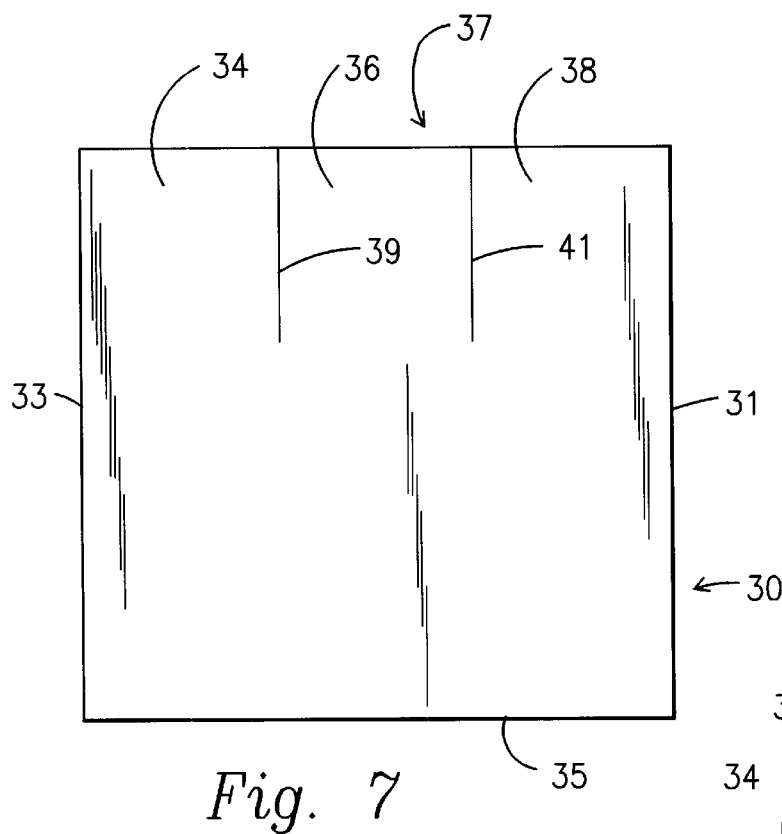
FIG. 7 shows a sheet of flexible bio-compatible material having two slits therein and which will be employed to create a replacement aortic valve tri-cuspid.

With reference to FIG. 5, two such star-shaped members, modified as shown in FIG. 4 may be interconnected together by engaging their respective outwardly directed points 17 and welding them together using any suitable technique. As shown in FIG. 5, each star-shaped member 15 has its inwardly directed points 19 free and unattached.

With reference to FIG. 6, a plurality of pairs of star-shaped members 15 such as the pair illustrated in FIG. 5 may be interconnected together by interconnecting pairs of inwardly directed points 19 through any suitable means such as welding to form the structure 20 illustrated in FIG. 6 and consisting of three such pairs of star-shaped members 15 interconnected together.

Figure 8:
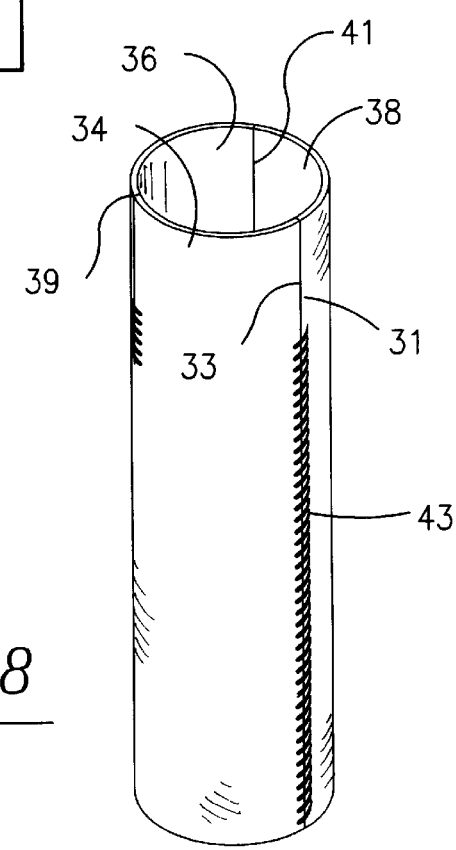
FIG. 8 shows the sheet of FIG. 7 with the open edges thereof sewn together to form a tube.

With reference to FIGS. 7–10, a sheet 30 of a flexible bio-compatible material such as, for example, silk, DACRON, NYLON, polytetrafluoroethylene or polyurethane is formed in a rectangular shape including sides 31, 33, a bottom wall 35, and a top wall 37 in which two slits 39 and 41 are formed to define three flaps 34, 36 and 38. With reference to FIG. 8, the sides 31 and 33 are abutted together and are attached through a technique such as, for example, sewing, employing the thread 43 as shown. Thereafter, with reference to FIG. 9, the three flaps 34, 36 and 38 formed by the slits 39 and 41 are folded in overlapping fashion as seen in FIG. 9 to form a replacement aortic valve tri-cuspid device 45.

With reference to FIG. 10, the device 45 may be inserted within the three pairs of star-shaped members 15 assembled together as illustrated in FIG. 6 and described hereinabove and may be affixed therein through sewing at 47 that attaches the members 15 at the area of the inwardly directed points 19 as shown. The device so assembled is designated in FIG. 10 by the reference numeral 50.

Figures 14, 15:
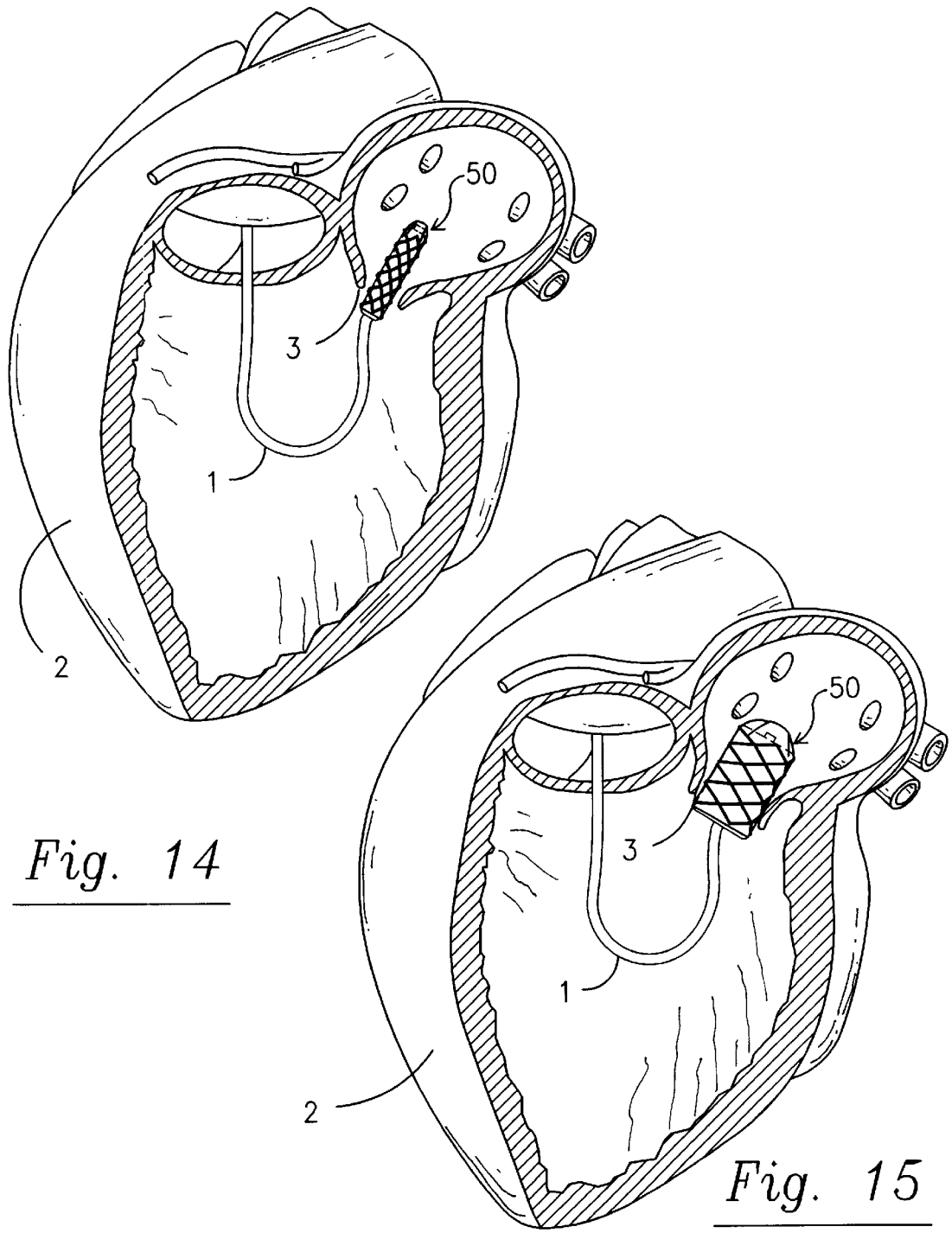
FIG. 14 shows the assembly of FIG. 10 as inserted, through the use of a catheter, within an aortic opening of a heart.
FIG. 15 shows the assembly of FIG. 14 but with the device of FIG. 9 inflated through the use of the catheter so that the entire assembly expands to fill the aortic opening shown.
Figure 16:
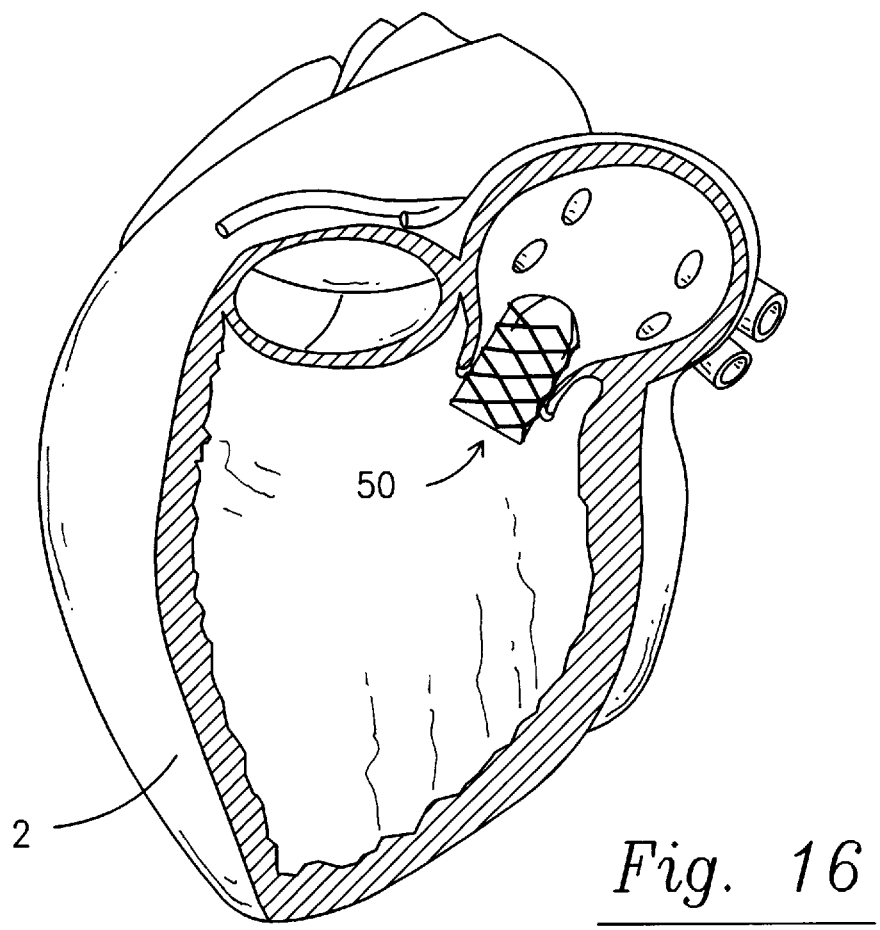
FIG. 16 shows the assembly of FIG. 15 remaining in place after the catheter has been removed therefrom.

With reference to FIGS. 14, 15 and 16, the device 50 is attached to a catheter 1 and is inserted into an opening 3 in the aortic valve area within the heart 2. As shown in FIG. 15, the catheter 1 is employed to inflate the device 50 so that it fills the opening 3. During this inflation process, the individual star-shaped members 15 are further deformed from their orientation as seen in FIG. 10 and this deformation is maintained once the catheter 1 is removed as shown in FIG. 16 to maintain the device 45 in the expanded state shown to obscure the opening 3 and provide a replacement aortic tri-cuspid valve.

Figure 11:
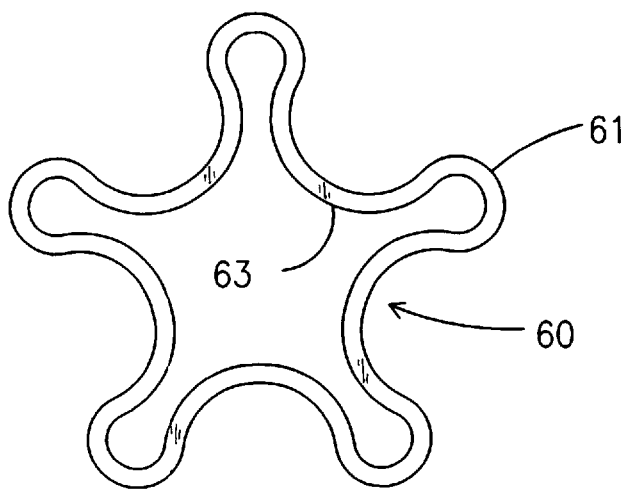
FIGS. 11, 12 and 13 show alternative constructions for the star-shaped members.
Figure 12:
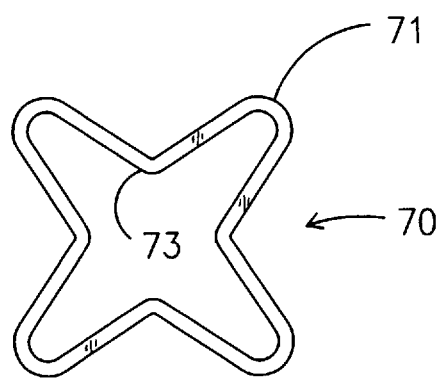
Figure 13:
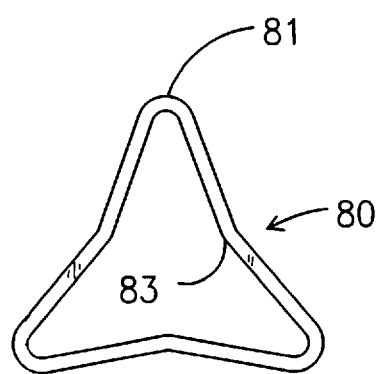

FIGS. 11, 12 and 13 show alternative constructions for the star-shaped member. Thus, FIG. 11 shows a star-shaped member 60 that consists of five arcuately shaped outwardly directed points 61 and five arcuate inwardly directed portions 63. FIG. 12 shows a four pointed star-shaped member 70 having four arcuately shaped outwardly directed points 71 and four inwardly directed points 73. FIG. 13 shows a three pointed star-shaped member 80 having three outwardly directed points 81 and three inwardly directed points 83. Each of the members 60, 70 or 80 may be employed in the same manner described hereinabove as is the case with the star-shaped member 15. Each of the members 60, 70 or 80 may be formed from a metal sheet such as the metal sheet 10 illustrated in FIG. 1 and employing the same process illustrated in FIG. 2. Each of these members 60, 70 or 80 may be manipulated in the manner described in FIGS. 4, 5 and 6.

Figures 17, 18:
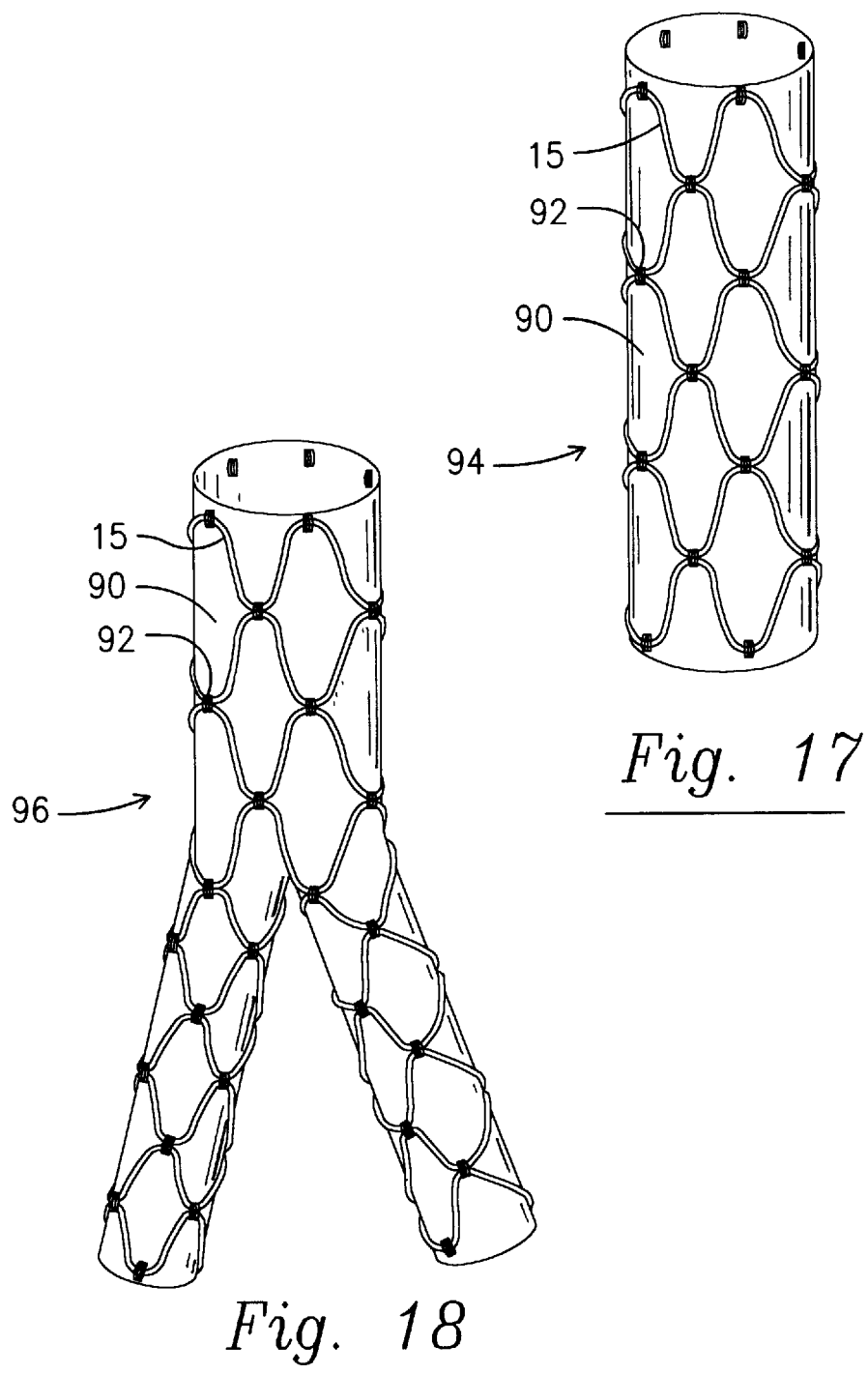
FIG. 17 shows a tubular structure of a knitted, woven, or extruded synthetic material to which is sutured a chain of stents.
FIG. 18 shows a structure similar to FIG. 17 but formed in a shape for use in a bifurcated artery.
Figure 19:
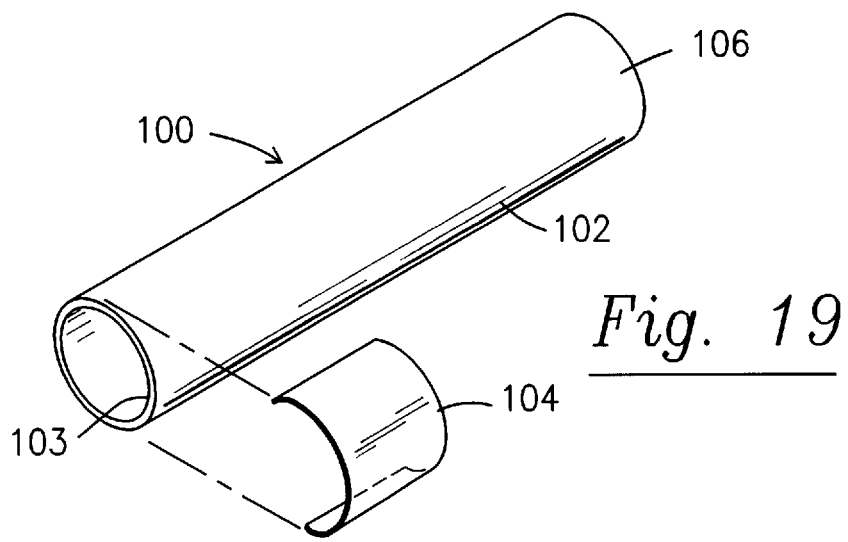
FIG. 19 shows a bio-compatible conduit about to receive a patch made from a like bio-compatible material.

In FIGS. 17 and 18 a tube 90 made from knitted, woven or an extruded bio-compatible polymer has a chain of stents 15 sutured 92 to the tube 90. This single graft 94 or the bifurcated graft 96 resulting from the joining of the tube 90 and the stents 15 can be used to replace a diseased portion of an artery in various locations including the heart.

Figure 20:
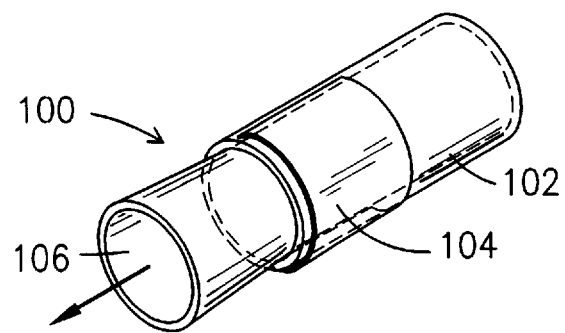
FIG. 20 shows the patch sutured to the outside of the conduit.
Figure 21:
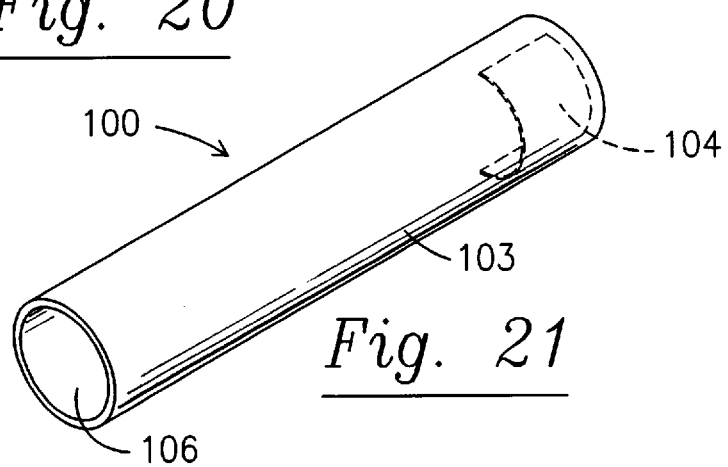
Figure 22:
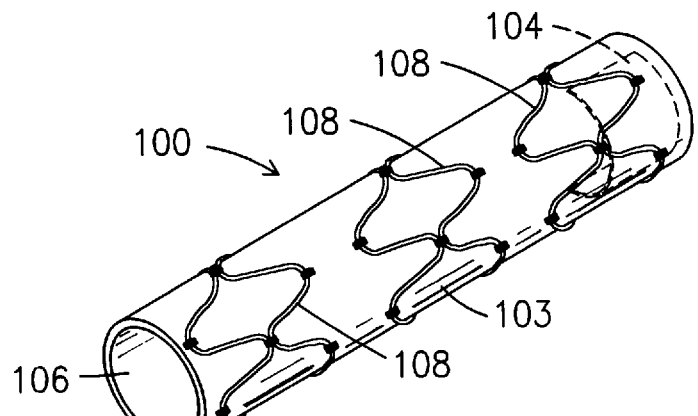
FIG. 22 shows the conduit of FIG. 21 with a stent sutured to the exterior surface.
Figure 23:
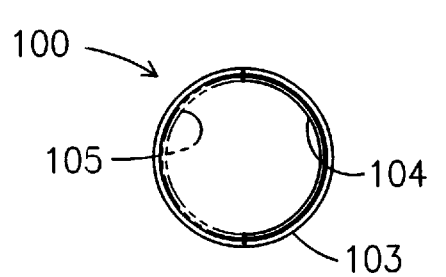
FIG. 23 shows an end view of the conduit of FIG. 21.

An alternate process for preparing a stent graft according to this invention shown in FIGS. 19–25, employs a conduit 100 made from a bovine or synthetic bio-compatible material such as polytetrafluoroethylene, DACRON® or a polyester coated with an anticoagulant such as warfarin or heparin. A single patch 104 is sutured to the exterior 102 of conduit 100. Thereafter, end 106 is pulled inside the conduit 100 as shown in FIG. 20 so that the patch 104 ends up on the inside of the conduit 100 as shown in phantom in FIG. 21. A stent 108 as described in the specification previously as stent 15 is thereafter sutured to the exterior 103 of conduit 100. The single patch 104 acts as a valve as seen in FIG. 23. The blockage of blood flow is shown in phantom with the patch 104 identified as 105 when it acts to block blood flow through the conduit 100.

Figure 24:
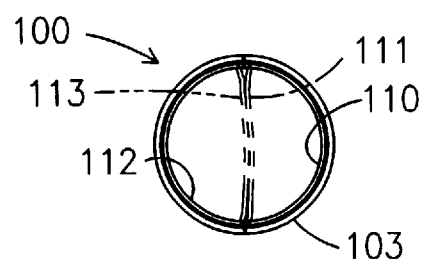
FIG. 24 shows an end view of a conduit with two patches.

Patches 110 and 112 can be sutured to conduit 100 in like manner to patch 104 to form a bicuspid valve as shown in FIG. 24. When patches 110 and 112 are closed (identified now as 111 and 113, respectively) the block flow of blood through conduit 100.

Figure 25:
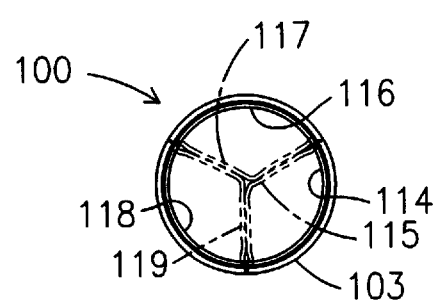
FIG. 25 shows an end view of a conduit with three patches.

Patches 114, 116 and 118 can be sutured to conduit 100 in like manner to patch 104 to form a tricuspid valve as shown in FIG. 25. When patches 114, 116 and 118 are closed (identified now as 115, 117, and 119, respectively) they block flow of blood through conduit 100.

As such, an invention has been described in terms of a preferred embodiment thereof which fulfills each and every one of the objects of the invention as set forth hereinabove and provides a new and useful star-shaped stent and replacement valve for use in repairing a damaged cardiac valve of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:

1. A stent comprising:
    a) a plurality of star-shaped members, each including:
        i) a plurality of outwardly directed points and an equal plurality of inwardly directed points;
        ii) an open center;
        iii) said outwardly directed points being bent and facing away from a plane defined by said inwardly directed points;
    b) said star-shaped members being connected together.

2. The stent of claim 1, wherein said star-shaped members are connected together by a connection that fastens at least one outwardly directed point of one star-shaped member with a corresponding outwardly directed point of an adjacent star-shaped member.

3. The stent of claim 1, wherein said star-shaped members are connected together by a connection that fastens at least one inwardly directed point of one star-shaped member with a corresponding inwardly directed point of an adjacent star-shaped member.

4. The stent of claim 2, wherein adjacent said star-shaped members form a pair of star-shaped members, and further including two pairs of star-shaped members being fastened together by a connection that fastens at least one inwardly directed point of one star-shaped member of one such pair with a corresponding inwardly directed point of one star-shaped member of an adjacent pair.

5. The stent of claim 3, wherein adjacent said star-shaped members form a pair of star-shaped members, and further including two pairs of star-shaped members being fastened together by a connection that fastens at least one outwardly directed point of one star-shaped member of one such pair with a corresponding outwardly directed point of one star-shaped member of an adjacent pair.

6. The stent of claim 1, wherein each star-shaped member has five outwardly directed points and five inwardly directed points.

7. The stent of claim 1, wherein each star-shaped member has four outwardly directed points and four inwardly directed points.

8. The stent of claim 1, wherein each star-shaped member has three outwardly directed points and three inwardly directed points.

9. The stent of claim 4, further including a replacement aortic valve tri-cuspid fastened within said pairs of star-shaped members.

10. The stent of claim 9, wherein said replacement aortic valve tri-cuspid includes a tubular body.

11. A method of making a stent-valve including the steps of:
   a) forming a bio-compatible cylindrical conduit and suturing a patch of a bio-compatible substance to an exterior surface of the conduit;
   b) pulling an end of the conduit inside the conduit until the patch is located on an interior surface of the conduit with the former exterior surface of the conduit now the interior surface;
   c) suturing a plurality of stents according to claim 1 to the exterior surface of the conduit; and
   d) deploying the patch on the inside surface of the conduit to form a mono-cuspid valve.

12. The method according to claim 11 wherein two patches are sutured spaced apart to the exterior surface of the conduit in step a) so that a bicuspid valve is formed.

13. The method according to claim 11 wherein three patches are sutured spaced apart to the exterior surface of the conduit in step a) so that a tricuspid valve is formed.

14. The method according to claim 11 wherein an anticoagulant is coated on the conduit and patch to prevent clotting around the valve.

15. A method of making a stent including the steps of:
   a) forming a plurality of flat star-shaped members each including a plurality of outwardly directed points and an equal plurality of inwardly directed points and an open center;
   b) bending said outwardly directed points so that they face away from a plane defined by said inwardly directed points;
   c) fastening said star-shaped members together.

16. The method of claim 15, wherein said fastening step includes the step of connecting said star-shaped members together by fastening at least one outwardly directed point of one star-shaped member with a corresponding outwardly directed point of an adjacent star-shaped member.

17. The method of claim 15, wherein said fastening step includes the step of connecting said star-shaped members together by fastening at least one inwardly directed point of one star-shaped member with a corresponding inwardly directed point of an adjacent star-shaped member.

18. The method of claim 16, wherein adjacent said star-shaped members form a pair of star-shaped members, and said method further including the step of fastening two pairs of star-shaped members together by fastening at least one inwardly directed point of one star-shaped member of one such pair with a corresponding inwardly directed point of one star-shaped member of an adjacent pair.

19. The method of claim 17, wherein adjacent said star-shaped members form a pair of star-shaped members, and said method further including the step of fastening two pairs of star-shaped members together by fastening at least one outwardly directed point of one star-shaped member of one such pair with a corresponding outwardly directed point of one star-shaped member of an adjacent pair.

20. The method of claim 15, wherein said forming step includes the step of forming a plurality of flat star-shaped members each having five outwardly directed and five inwardly directed points.

21. The method of claim 18, further including the step of fastening a replacement aortic valve tri-cuspid within said pairs.

22. The method of claim 19, wherein adjacent said star-shaped members form a pair of star-shaped members, and said method further including the step of fastening two pairs of star-shaped members together by fastening at least one inwardly directed point of one star-shaped member of one such pair with a corresponding inwardly directed point of one star-shaped member of an adjacent pair.

23. The method of claim 15 wherein the plurality of flat-star shaped members are derived from cutting a flat metal sheet of a material selected from the group consisting of stainless steel, titanium, elgiloy or NITINOL.

24. A stent comprising:
   a) a plurality of star-shaped members, each including:
      i) five outwardly directed points and five inwardly directed points;
      ii) an open center;
      iii) said outwardly directed points being bent and facing away from a plane defined by said inwardly directed points;
   b) said star-shaped members being connected together in a plurality of pairs;
   c) two pairs of star-shaped members being fastened together by a connection fastening at least one inwardly or outwardly directed point of one star-shaped member of one such pair with a corresponding inwardly or outwardly directed point of one star-shaped member of an adjacent pair;
   d) a replacement aortic valve tri-cuspid fastened within said pairs of star-shaped members and including a tubular body.

25. The stent according to claim 24 wherein the star-shaped members are sutured to the tubular body.

26. The stent according to claim 25 wherein the tubular body is bifurcated.

27. The stent according to claim 24 wherein the tubular body is a knitted, woven or extruded polymeric material acceptable to living tissue.

* * * * *